(12) United States Patent
Richard et al.

(10) Patent No.: US 10,299,778 B2
(45) Date of Patent: May 28, 2019

(54) SURGICAL ACCESS DEVICE INCLUDING GIMBAL MOUNT COOPERATING WITH BELLOWS

(71) Applicant: Covidien LP, Mansfield, MA (US)

(72) Inventors: Craig Richard, Shelton, CT (US); Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 129 days.

(21) Appl. No.: 13/861,428

(22) Filed: Apr. 12, 2013

(65) Prior Publication Data

US 2013/0310773 A1 Nov. 21, 2013

Related U.S. Application Data

(60) Provisional application No. 61/647,008, filed on May 15, 2012.

(51) Int. Cl.
| | | |
|---|---|---|
| *A61B 17/02* | (2006.01) | |
| *A61B 17/34* | (2006.01) | |
| *A61M 39/06* | (2006.01) | |

(52) U.S. Cl.
CPC .......... *A61B 17/0218* (2013.01); *A61B 17/02* (2013.01); *A61B 17/3423* (2013.01);
(Continued)

(58) Field of Classification Search
CPC . A61B 17/3423; A61B 17/3462; A61B 17/02; A61B 17/0218; A61B 2017/3425;
(Continued)

(56) References Cited

U.S. PATENT DOCUMENTS 5,073,169 A * 12/1991 Raiken ................... A61B 17/34
604/174
5,628,732 A * 5/1997 Antoon, Jr. ........ A61B 17/3462
604/167.06
(Continued)

FOREIGN PATENT DOCUMENTS

| EP | 0 638 290 A1 | 2/1995 |
| EP | 2 229 897 A1 | 9/2010 |

(Continued)

OTHER PUBLICATIONS

Extended European Search Report dated Sep. 19, 2013 for EP 13 16 7615.
European Search Report for EP 13 16 7618 dated Jun. 14, 2013.

*Primary Examiner* — Kevin T Truong
*Assistant Examiner* — Amy R Sipp

(57) ABSTRACT

A surgical access device includes a seal assembly having a seal housing and a gimbal mount disposed within the seal housing, the seal housing defining a central longitudinal axis and having a longitudinal passage for receiving at least one surgical object therethrough and the gimbal mount adapted for angular movement relative to the central longitudinal axis. The surgical access device also includes a bellows configured to engage at least a portion of the gimbal mount, the bellows dimensioned and adapted to establish a biasing relationship with the gimbal mount, such that the bellows overcomes a frictional relationship between the gimbal mount and the seal housing, thereby moving the gimbal mount towards a position in which the passage of the gimbal mount is aligned with the central longitudinal axis. The bellows is configured to be attached to a side wall of the seal housing.

19 Claims, 13 Drawing Sheets

(52) U.S. Cl.
CPC ...... *A61B 17/3462* (2013.01); *A61B 17/3498* (2013.01); *A61M 39/06* (2013.01); *A61B 2017/3425* (2013.01); *A61B 2017/3427* (2013.01)

(58) Field of Classification Search
CPC ........ A61B 2017/3427; A61B 17/3498; A61B 2017/3464; A61B 2017/3466; Y10T 403/32713; Y10T 403/32811
USPC ....... 600/201–210, 215; 604/167.01–167.06; 403/132, 144
See application file for complete search history.

(56) References Cited

U.S. PATENT DOCUMENTS

| | | |
|---|---|---|
| 5,720,759 A | 2/1998 | Green et al. |
| 5,792,113 A * | 8/1998 | Kramer et al. .......... 604/167.01 |
| 5,820,600 A * | 10/1998 | Carlson .............. A61B 17/3462 |
| | | 251/149.2 |
| 7,044,974 B2 * | 5/2006 | Garber et al. ............. 623/22.21 |
| 7,582,071 B2 | 9/2009 | Wenchell |
| 7,632,250 B2 | 12/2009 | Smith et al. |
| 7,896,847 B2 | 3/2011 | Wenchell |
| 7,931,624 B2 | 4/2011 | Smith et al. |
| 7,951,118 B2 | 5/2011 | Smith et al. |
| 2004/0068232 A1 | 4/2004 | Hart et al. |
| 2004/0204682 A1 | 10/2004 | Smith |
| 2005/0212221 A1 * | 9/2005 | Smith ................ A61B 17/3462 |
| | | 277/628 |
| 2006/0224120 A1 | 10/2006 | Smith et al. |
| 2007/0255218 A1 * | 11/2007 | Franer ................ A61B 17/3462 |
| | | 604/167.02 |
| 2008/0125716 A1 | 5/2008 | Cruz |
| 2009/0221966 A1 | 9/2009 | Richard |
| 2010/0049138 A1 * | 2/2010 | Smith ................ A61B 17/3462 |
| | | 604/167.01 |
| 2010/0228094 A1 | 9/2010 | Ortiz et al. |
| 2011/0124972 A1 | 5/2011 | Wenchell |
| 2011/0196207 A1 | 8/2011 | Smith et al. |
| 2011/0201891 A1 | 8/2011 | Smith et al. |

FOREIGN PATENT DOCUMENTS

| | | |
|---|---|---|
| EP | 2 233 090 A1 | 9/2010 |
| WO | WO 97/42991 A1 | 11/1997 |
| WO | WO 03/094760 A2 | 11/2003 |
| WO | WO 2007/121425 A1 | 10/2007 |

* cited by examiner

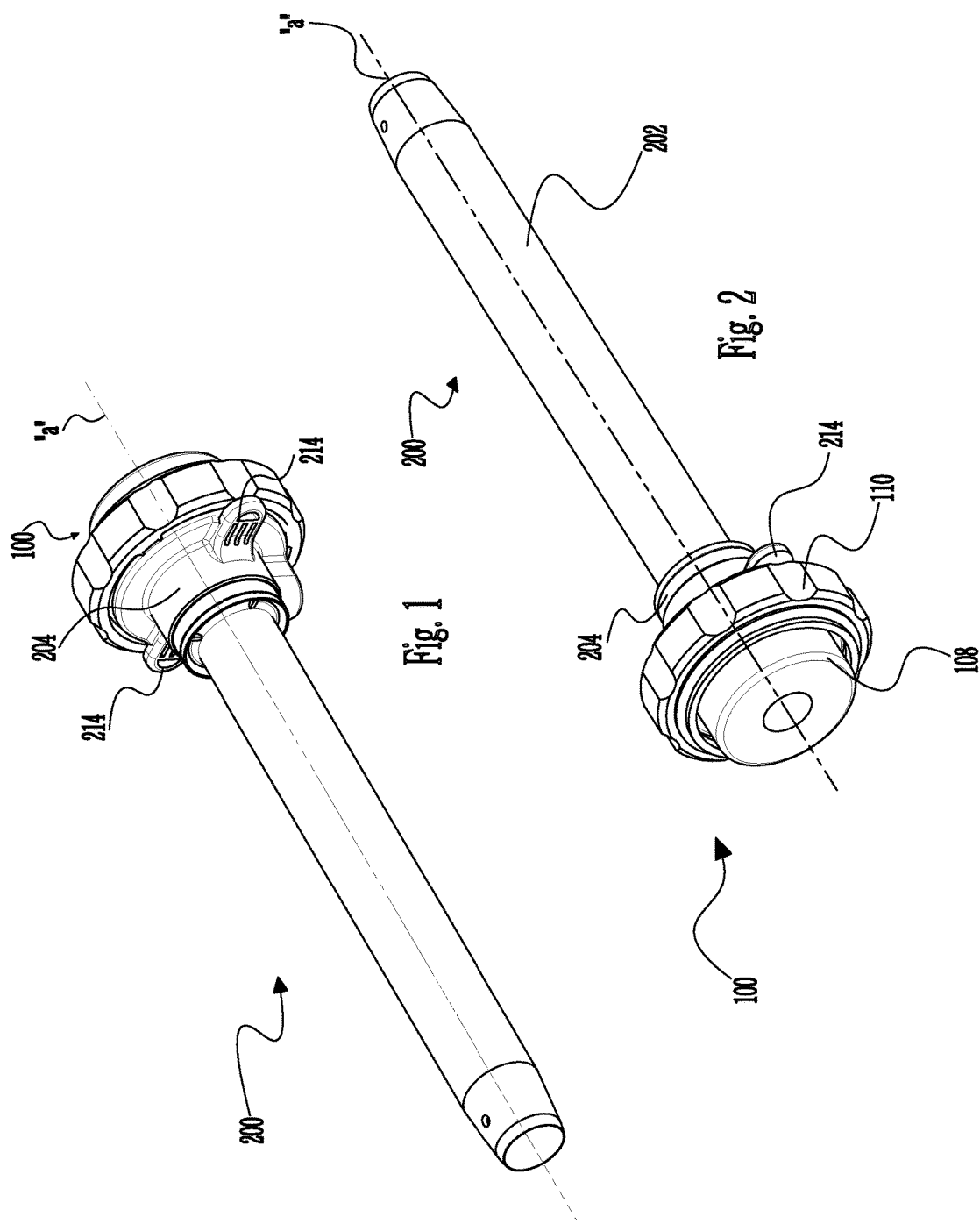

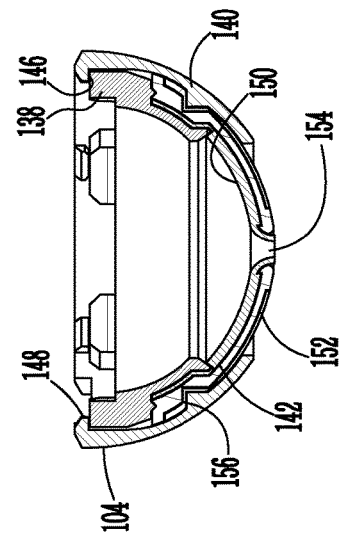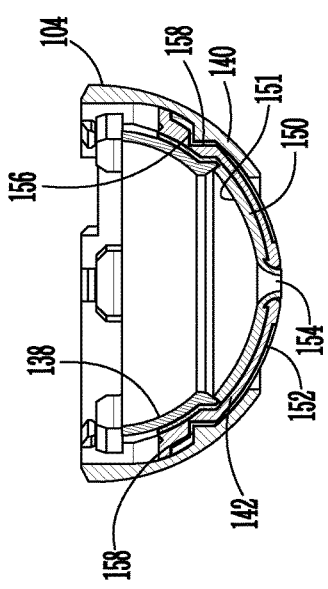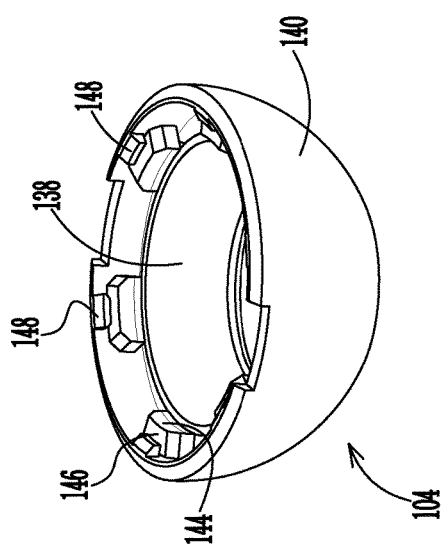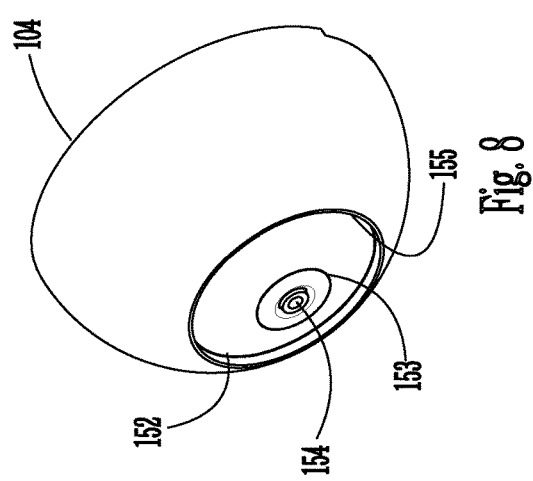

SURGICAL ACCESS DEVICE INCLUDING GIMBAL MOUNT COOPERATING WITH BELLOWS

CROSS REFERENCE TO RELATED APPLICATION

The present application claims the benefit of and priority to U.S. Provisional Application Ser. No. 61/647,008, filed on May 15, 2012, the entire contents of which are incorporated herein by reference.

BACKGROUND

Technical Field

The present disclosure relates to a seal system adapted to permit the introduction of surgical instrumentation into a patient's body. In particular, the present disclosure relates to a seal system for use with an introducer or access device, which is intended for insertion into a patient's body, and to receive an instrument in sealing engagement therewith.

Background of Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere.

In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

According to one aspect of the present disclosure, a surgical access device is provided. The surgical access device includes a seal assembly including a seal housing and a gimbal mount disposed within the seal housing, the seal housing defining a central longitudinal axis and having a longitudinal passage for receiving at least one surgical object therethrough and the gimbal mount adapted for angular movement relative to the central longitudinal axis. The surgical access device also includes a bellows configured to engage at least a portion of the gimbal mount. The bellows is configured to be attached to a side wall of the seal housing.

In previous seal arrangements, when a movable valve is in a position in which its longitudinal passage is mis-aligned with the central longitudinal axis, friction that exists between the valve, e.g., a gimbal mount, and the seal housing prevents the longitudinal passage of the valve from aligning with the central longitudinal axis. When this occurs, insertion of instruments through the valve is more likely to tear or otherwise damage the valve, because the sharp tip of such an instrument engages the elastomeric material adjacent to the passage, rather than passing directly through the passage, or else engages the elastomeric material too far from the passage such that the valve is unable to move sufficiently before being torn. By biasing the longitudinal passage of the seal assembly towards the central longitudinal axis, the bellows overcomes the frictional relationship that exists between the gimbal mount and the seal housing, and thereby may decrease the likelihood that the gimbal mount will be damaged during use. In addition, the use of a bellows provides an additional sealing benefit, as insufflation gas is prevented by the bellows from escaping between the gimbal mount and the seal housing. Attaching the bellows to the sidewall of the seal housing also decreases or eliminates the need for additional spacing within the seal housing in a location proximal to the gimbal mount, thereby enabling the height of the seal housing to be reduced. Still further, the bellows provides a relatively small amount of biasing force to the gimbal mount—such a small force may be advantageous when a surgeon is using the device. More specifically, the bellows provides for a biasing force that is large enough to enable the benefits of self-centering the gimbal mount, but small enough such that manipulation of an instrument within the seal won't cause the passage of the seal to become "cat-eyed" or stretched to a degree that would cause leakage.

In one exemplary embodiment, the gimbal mount defines a substantially hemispherical configuration. In another exemplary embodiment, the gimbal mount defines a substantially parabolic configuration.

In yet another exemplary embodiment, the seal assembly includes an upper housing portion and a lower housing portion, the upper housing portion mechanically cooperating with the bellows. The upper seal housing defines an angular opening therethrough to facilitate angular reception of the at least one surgical object.

In another exemplary embodiment, the rubber bellows has a uniform wall thickness of about 0.01 inches. The rubber bellows includes an inner wall and an outer wall, the inner and outer walls configured to be substantially equal in length.

Moreover, in an alternative embodiment, the rubber bellows includes an inner wall and an outer wall, the inner wall having a first length and the outer wall having a second length, where the first length is greater than the second length. Additionally, the rubber bellows are positioned within a space such that the gimbal mount is movable relative to the seal housing, the space defined between an inner wall and an outer wall of the seal housing.

In one exemplary embodiment, the rubber bellows is dimensioned and configured to create a plurality of sealing points between the seal housing and the gimbal mount.

In another exemplary embodiment, the seal housing is disposed in mechanical cooperation with a cannula assembly. Moreover, the cannula assembly may detachably connect to the gimbal mount via a plurality of sealing points.

In yet another exemplary embodiment, the cannula assembly includes a duck bill seal configured to receive the gimbal mount and prevent loss of insufflation gas when no surgical object is inserted through the longitudinal passage of the seal housing.

Additionally, the duck bill seal is dimensioned and configured to directly seal the cannula assembly to the gimbal mount. The duck bill seal is dimensioned and configured to be tapered to allow the cannula assembly to have a reduced diameter. Moreover, the seal housing is adapted to be detachably mounted to a cannula housing of the cannula assembly including the duck bill seal for providing a substantially fluid-tight seal when at least one surgical object is inserted into the seal assembly and through the cannula assembly.

In another aspect of the present disclosure, a cannula assembly is provided. The cannula assembly includes a cannula housing, a cannula sleeve extending distally from the cannula housing and a seal assembly disposed in mechanical cooperation with the cannula housing. The seal assembly includes a seal housing and a gimbal mount disposed within the seal housing, the seal housing defining a central longitudinal axis and having a longitudinal passage for receiving at least one surgical object therethrough and the gimbal mount adapted for angular movement relative to the central longitudinal axis. The seal housing also includes a bellows configured to engage at least a portion of the gimbal mount. The bellows is configured to be attached to a side wall of the seal housing.

In one exemplary embodiment, the gimbal mount includes at least a first gimbal housing and a second gimbal housing welded together at a plurality of points.

In another exemplary embodiment, the gimbal mount includes at least a first gimbal housing and a second gimbal housing interconnected with twist locking features. The rubber bellows deforms around the twist locking features.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 1-2 are perspective views of a cannula assembly and a seal assembly;

FIGS. 7-8 are top and bottom perspective views of the gimbal mount of the seal assembly, in accordance with the embodiments of FIGS. 4A-6B;

FIGS. 9-10 are cross-sectional views of the gimbal mount, in accordance with the embodiments of FIGS. 4A-8;

Figure 3:
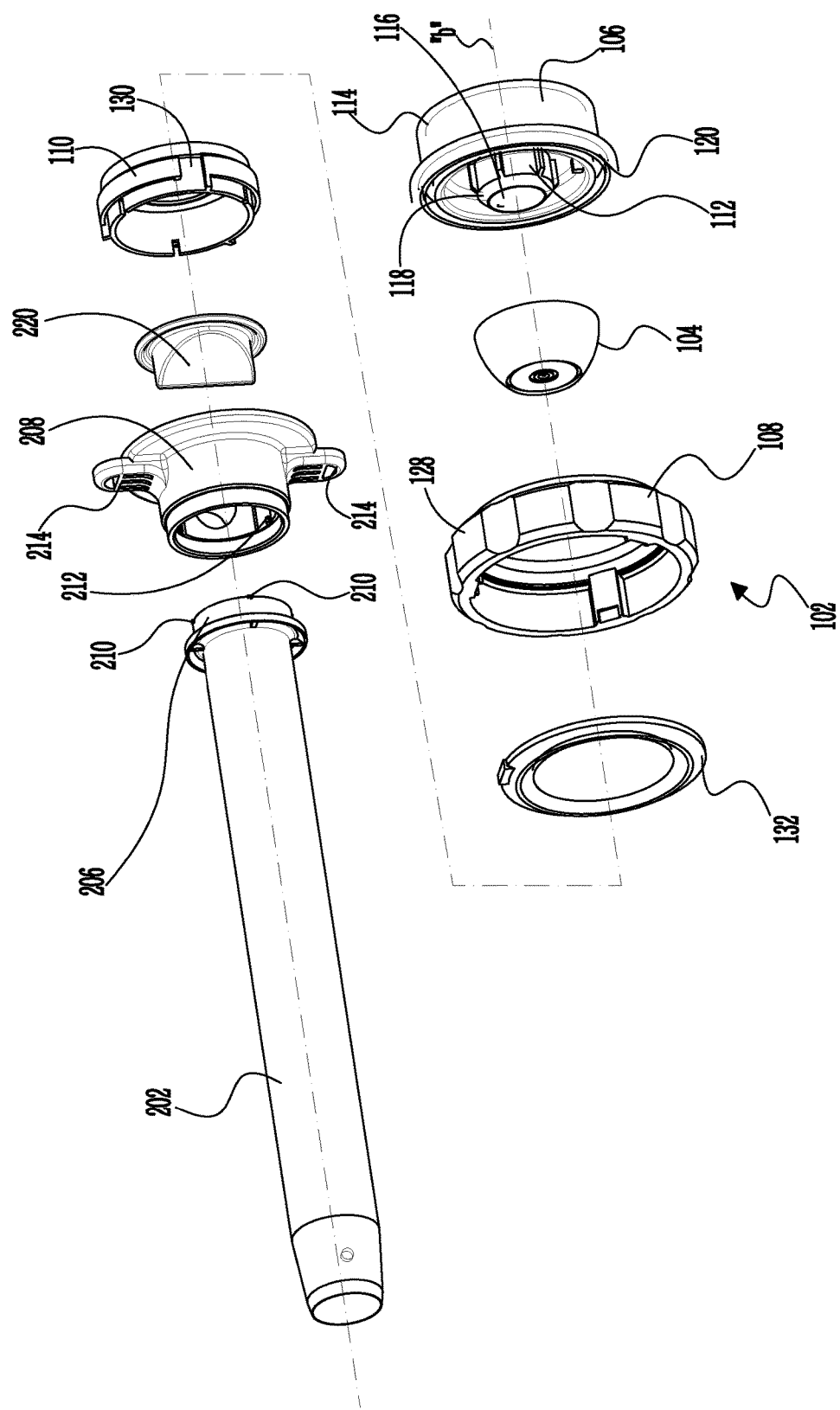
FIG. 3 is a perspective view with parts separated of the cannula and seal assemblies of FIGS. 1-2.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown), which is a sharp pointed instrument positionable within the passageway of the cannula assembly 200. The obturator assembly is utilized to penetrate the abdominal wall and then subsequently be removed from the cannula assembly to permit introduction of the surgical instrumentation utilized to perform the procedure.

Cannula assembly 200 includes cannula sleeve 202 and cannula housing 204 mounted to an end of the sleeve 202. Cannula sleeve 202 defines a longitudinal axis "a" extending along the length of sleeve 202. Sleeve 202 further defines an internal longitudinal passage dimensioned to permit passage of surgical instrumentation. Sleeve 202 may be formed of stainless steel or other rigid materials, such as a polymeric material or the like. Sleeve 202 may be clear or opaque. The diameter of sleeve 202 may vary, but typically ranges from 10 to 15 mm for use with the seal assembly 100 of the present disclosure.

Cannula housing 204 includes two components, specifically, housing flange 206, which is attached to the proximal end of cannula sleeve 202 and main housing 208, as shown in FIG. 3. Main housing 208 is connectable to housing flange 206 through a bayonet coupling consisting of radially spaced tongues 210 on the exterior of housing flange 206 and corresponding recesses 212 within the interior of main housing 208. Tongues 210 are receivable within recesses 212. Thereafter, housing flange 206 and main housing 208 are rotated to securely lock the tongues 210 within the recesses 212. Other conventional means, e.g., a snap fit, ultrasonic welding or any other means envisioned by one skilled in the art including, e.g., adhesive means, may be incorporated to connect housing flange 206 and main housing 208. Main housing 208 further includes diametrically opposed housing grips 214 dimensioned and arranged for gripping engagement by the fingers of the user. Although shown and described as two components, cannula housing 204 may be a single component and attached to cannula sleeve 202 by any of the aforementioned means.

With reference to FIG. 3, in conjunction with FIGS. 1-2, cannula housing 204 further includes duck bill or zero closure valve 220, which tapers distally and inwardly to a sealed configuration as shown in the figure. Valve 220 opens to permit passage of the surgical instrumentation and closes in the absence of the instrumentation. Valve 220 is preferably adapted to close upon exposure to the forces exerted by the insufflation gases in the internal cavity. Other zero closure valves are also contemplated including single or multiple slit valve arrangements, trumpet valves, flapper valves, etc.

Referring again to FIG. 3, in conjunction with FIGS. 1-2, seal assembly 100 will be discussed in detail. Seal assembly 100 includes seal housing, generally identified as reference numeral 102, and gimbal mount 104, which is disposed within the seal housing 102. Seal housing 102 houses the sealing components of the assembly and defines the outer valve or seal body of the seal assembly 100. Seal housing 102 defines central seal housing axis "b," which is preferably parallel to the axis "a" of cannula sleeve 202 and, more specifically, coincident with the axis "a" of the cannula.

Seal housing 102 incorporates three housing components, namely, proximal, distal and lower housing components 106, 108, 110, respectively, which, when assembled together, form the seal housing 102. The proximal housing component 106 may also be referred to as the "upper housing portion," whereas the distal and lower housing components 108, 110 may also be referred to as "lower housing portions." Assembly of housing components 106, 108, 110 may be affected by any of the aforementioned connection means discussed with respect to cannula housing 204. Therefore, seal housing 102 may be considered as having an upper housing portion formed by component 106, and a detachable lower housing portion formed by components 108, 110.

Proximal housing component 106 defines inner guide wall 112 and outer wall 114 disposed radially outwardly of the inner guide wall 112. Inner guide wall 112 defines central passage 116, which is dimensioned to receive a surgical instrument and laterally confine the instrument within seal housing 102. Inner guide wall 112 is generally cylindrical in configuration and terminates in a distal arcuate surface 118. Outer wall 114 defines an annular recess 120 adjacent its distal end. Recess 120 receives annular lip 124 (see FIG. 17)

of distal housing component 108 to facilitate connection of the two components. As appreciated, proximal housing component 106 may also incorporate locking tabs, which engage corresponding structure of distal housing component 108 upon relative rotation of the components 106, 108 to securely connect the components.

Lower housing component 110 is disposed within the interior of distal housing component 108 and is securely connectable to the distal housing component 108 through a bayonet coupling. Such coupling includes radially spaced tongues 128, which depend radially inwardly to be received within correspondingly arranged grooves or recesses 130 on the exterior of lower housing component 110. Coupling of distal and lower housing components 108, 110 is thereby affected through simple rotation of the components.

Housing component 108 includes transverse wall 122 (see FIG. 18), inner cylindrical wall 124 depending in a proximal direction outwardly from the transverse wall 122 and outer wall 126 depending in a distal direction outwardly from the transverse wall 122. Inner cylindrical wall 124 is dimensioned to mate with outer wall 114 of proximal housing component 106, i.e., in a manner to be positioned within the interior of the outer wall 114 in frictional relation therewith.

With continued reference to FIG. 3, seal assembly 100 further includes skirt seal 132 mounted about the proximal end of lower housing component 110 or on the upper surface of the lower housing component 110 of the seal housing 102. Skirt seal 132 functions in minimizing the loss of insufflation gases through seal assembly 100. Stated differently, skirt seal 132 is adapted to prevent passage of fluids through seal assembly 100. Skirt seal 132 also engages gimbal mount 104 and serves to bias the gimbal mount 104 in a proximal direction against inner guide wall 112 of proximal housing component 106. Gimbal mount 104 is configured to rotate about central longitudinal axis "a" independent of the skirt seal 132. Additionally, skirt seal 132 may include an inner circumferential edge configured to slidably engage skirt seal 132. Skirt seal 132 is preferably fabricated from a suitable elastomeric material or the like to provide a spring-like characteristic sufficient to appropriately bias gimbal mount 104.

Figure 4A:
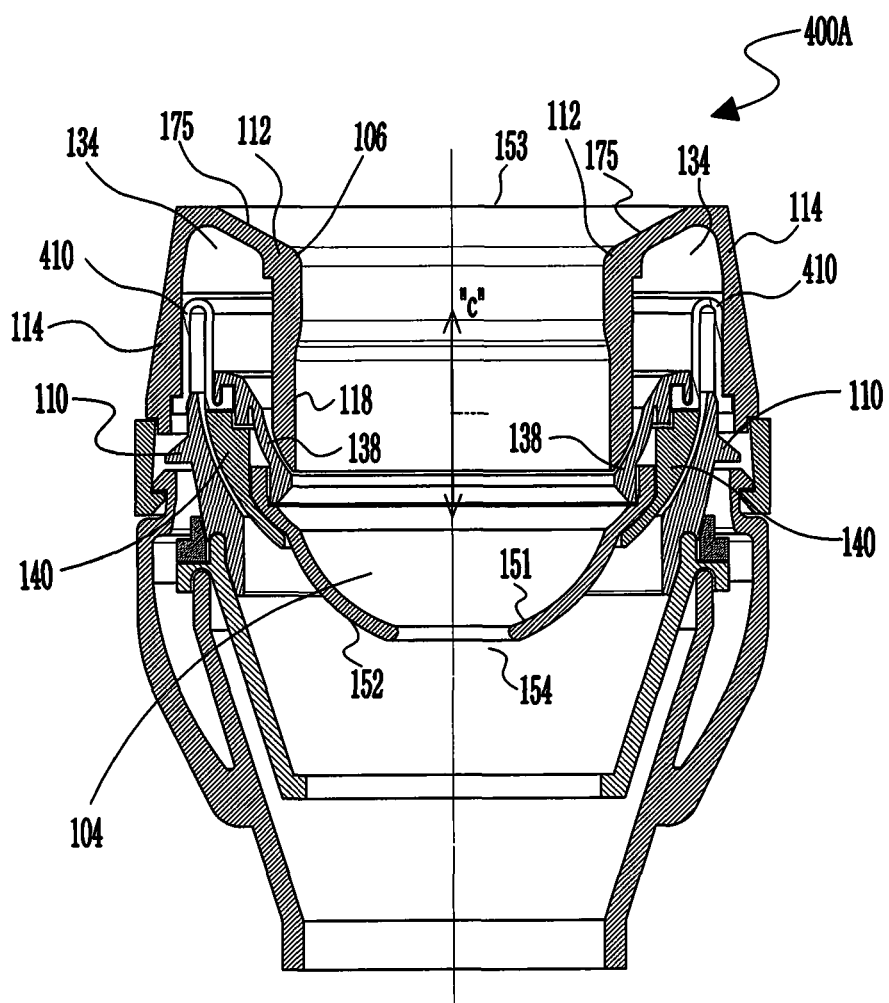
FIG. 4A is a side cross-sectional view of the cannula and seal assemblies illustrating the gimbal mount cooperating with the bellows in a first, unbiased position, in accordance with an embodiment of the present disclosure.

Referring to FIG. 4A, a side cross-sectional view 400A of the cannula and seal assemblies 100, 200 illustrating the gimbal mount 104 cooperating with bellows 410 (e.g., rubber bellows) in a first, unbiased position, in accordance with an embodiment of the present disclosure is presented.

Gimbal mount 104 is accommodated within an annular space 134 defined between inner and outer walls 112, 114 of proximal housing component 106 (see FIG. 3). Gimbal mount 104 is mounted in a manner that permits angulation of the gimbal mount 104 relative to seal axis "b." (see FIG. 3) Specifically, gimbal mount 104 is free to angulate about an axis or center of rotation "c" through a range of motion defined within the confines of annular space 134. An annular stop (not shown) may extend within annular space 134. Annular stop may be positioned to limit the degree of angulation of gimbal mount 104 if desired. The range of movement of gimbal mount 104 will be discussed in greater detail hereinbelow. Annular space 134 includes rubber bellows 410 for maintaining the gimbal mount 104 in a biased position when an instrument "i" (see FIGS. 17 and 18) is inserted through opening 153. It is contemplated that the rubber bellows 410 are some type of flexible or semi-rigid rubber structure for re-positioning the gimbal mount 104 in a substantially central position with respect to axes "a," "b," and "c," when the surgical instrument "i" is removed from the opening 153. Rubber bellows 410 may extend around the circumference or periphery of the top portion of the gimbal mount 104.

With further reference to FIG. 4A, gimbal mount 104 includes first and second gimbal housings 138, 140 and resilient seal member 142, which is mounted between the housings 138, 140. In a preferred arrangement, first and second gimbal housings 138, 140 and seal member 142 each define a substantially hemispherical configuration (see FIG. 6B). However, one skilled in the art may contemplate a gimbal mount 104 defining a substantially parabolic configuration (see FIG. 6A). First gimbal housing 138 is preferably seated within second gimbal housing 140 and secured to the second gimbal housing 140 through a snap fit connection or the like.

Seal member 142 of gimbal mount 104 is secured in interposed relation between first and second gimbal housings 138, 140. Seal member 142 preferably comprises a resilient center material (e.g., polyisoprene or natural rubber) with first and second layers of fabric 151, 152 impregnated on the respective proximal and distal surfaces of the resilient center material. Fabric may be of any suitable fabric for example, a SPANDEX® material containing about 20% LYCRA® and about 80% NYLON® available from Milliken®.

Figure 4B:
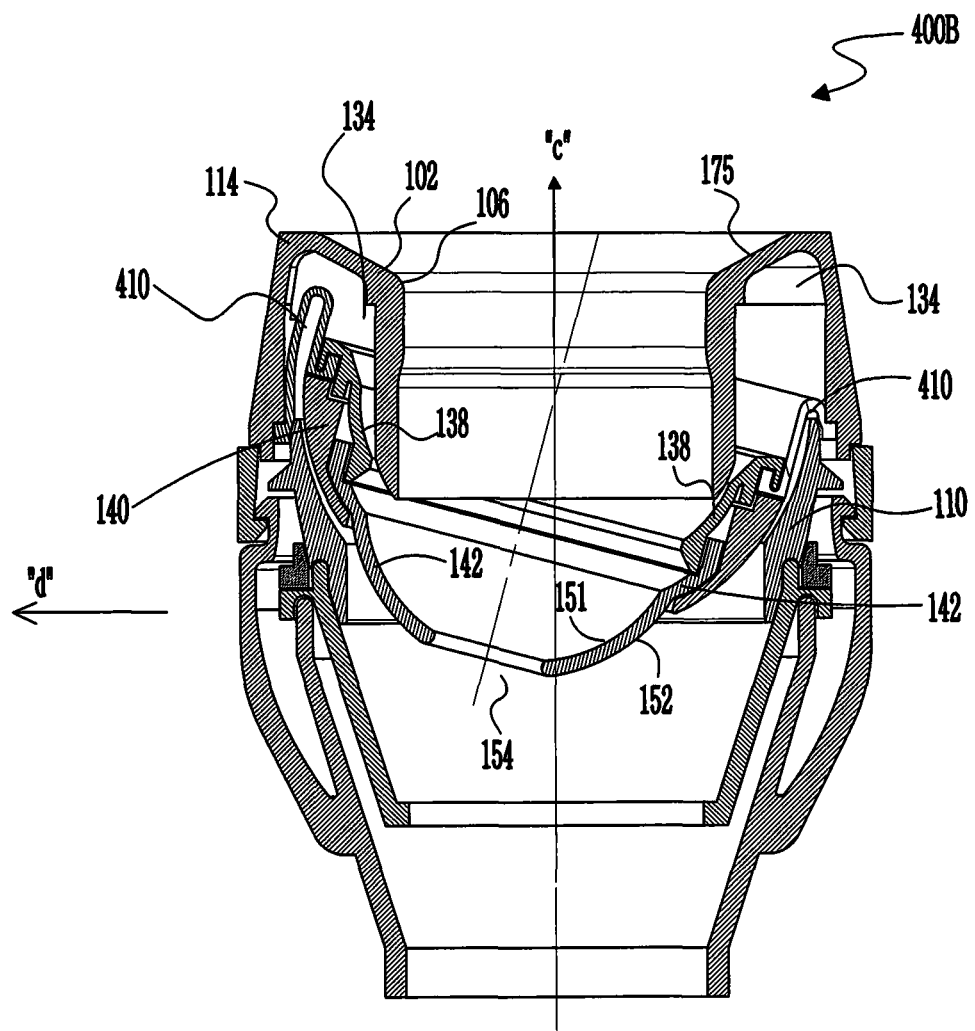
FIG. 4B is a side cross-sectional view of the cannula and seal assemblies illustrating the gimbal mount cooperating with the bellows in a second, biased position, in accordance with an embodiment of the present disclosure.

Seal member 142 defines central aperture 154 for sealed reception of a surgical instrument (see FIGS. 4A and 4B). In a preferred arrangement, first layer 151 is arranged to extend or overlap into aperture 154. In this manner, the fabric (which is stronger relative to the resilient material) is positioned to engage the surgical instrument upon passage through aperture 154 of seal member 142 thereby protecting the resilient material defining the aperture 154. This advantageously minimizes the potential of piercing, penetrating or tearing of the resilient material by the instrument.

Gimbal mount 104 is free to move within the annular space 134 defined between inner and outer walls 112, 114 and in cooperation with rubber bellows 410 to permit angulation of the instrument relative to the seal axis "b," while still maintaining a seal thereabout. Specifically, gimbal mount 104 is adapted for swiveling movement about a center of rotation "c," which is coincident with the axis "a" of seal assembly 100. In this regard, the axis "c" of the aperture 154 of seal member 142 intersects the axis "a" of the seal assembly 100 during angulation of the instrument, "i." During angulation, gimbal mount 104 is only in contact with seal housing 102 along distal arcuate surface 118 of proximal housing 106. Specifically, the arcuate inner surface of first gimbal housing 138 rides along distal arcuate surface 118 of inner wall 112 in contacting relation therewith to permit gimbal mount 104 to swivel within seal housing 102.

Additionally, the bellows 410 is attached or connected to a side wall of the seal housing 102. The bellows 410 seals the radially outer part of the gimbal mount 104 to the side wall of the seal housing 102 to prevent leakage, thus eliminating the need for an interface seal or skirt seal, as described above with reference to FIGS. 1-3. Thus, bellows 410 provides some self-centering that pushes or readjusts the gimbal mount 104 toward a centered, unbiased position, as shown in FIG. 4A.

Preferably, there is no other contact of gimbal mount 104 with any of the other components of seal housing 102, which thereby substantially minimizes resistance to the angulating movement. A lubricant may be provided between distal arcuate surface 118 and the inner surface of first gimbal housing 138 to facilitate angulation. In a preferred arrangement, gimbal mount 104 may angulate through an angle inclusive of about 30°, more preferably about 22.5° relative to seal housing axes "a" and "b."

Referring to FIG. 4B, is a side cross-sectional view 400B of the cannula and seal assemblies 100, 200 illustrating the gimbal mount 104 cooperating with rubber bellows 410 in a second, biased position, in accordance with an embodiment of the present disclosure is presented.

As shown, gimbal mount 104 has been biased in a direction "d." For example, a surgical instrument "i" (see FIGS. 17 and 18) may have been inserted through opening 153 of the cannula assembly 200 to force such bias. After the surgical instrument "i" has been removed from the cannula assembly 200, rubber bellows 410 enable gimbal mount 104 to move back to its original position (i.e., an unbiased position), as shown in FIG. 4A. The unbiased position is one where the gimbal mount 104 is centered with respect to axes "a," "b," and "c." Stated differently, rubber bellows 410 may force or propel or guide gimbal mount 104 to return to a position co-axial with the seal assembly 100. Thus, displacement of gimbal mount 104 from a substantially central position is negated by rubber bellows 410, once the surgical instrument "i" has been removed. Rubber bellows 410 may be moved or adjusted or displaced within the annular space 134 in order to re-position the gimbal mount 104 to a substantially central position with respect to the seal assembly 100.

Once again, bellows 410 is attached or connected to a side wall of the seal housing 102. The bellows 410 seals the radially outer part of the gimbal mount 104 to the side wall of the seal housing 102 to prevent leakage, thus eliminating the need for an interface seal or skirt seal, as described above with reference to FIGS. 1-3.

Figure 17:
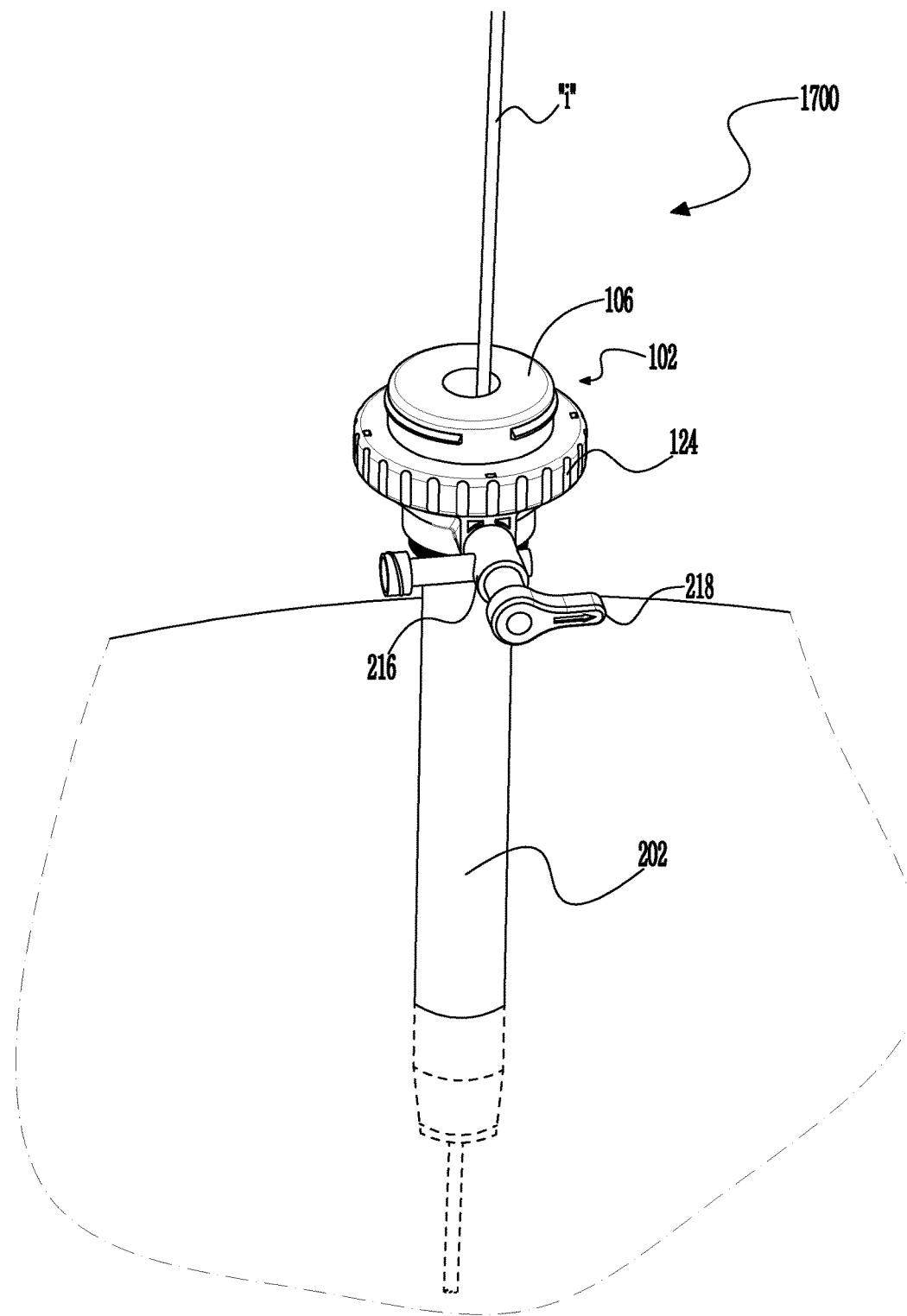
FIG. 17 is a perspective view illustrating the cannula assembly and seal assembly accessing an internal cavity with an instrument introduced therein, in accordance with the embodiments of the present disclosure.
Figure 18:
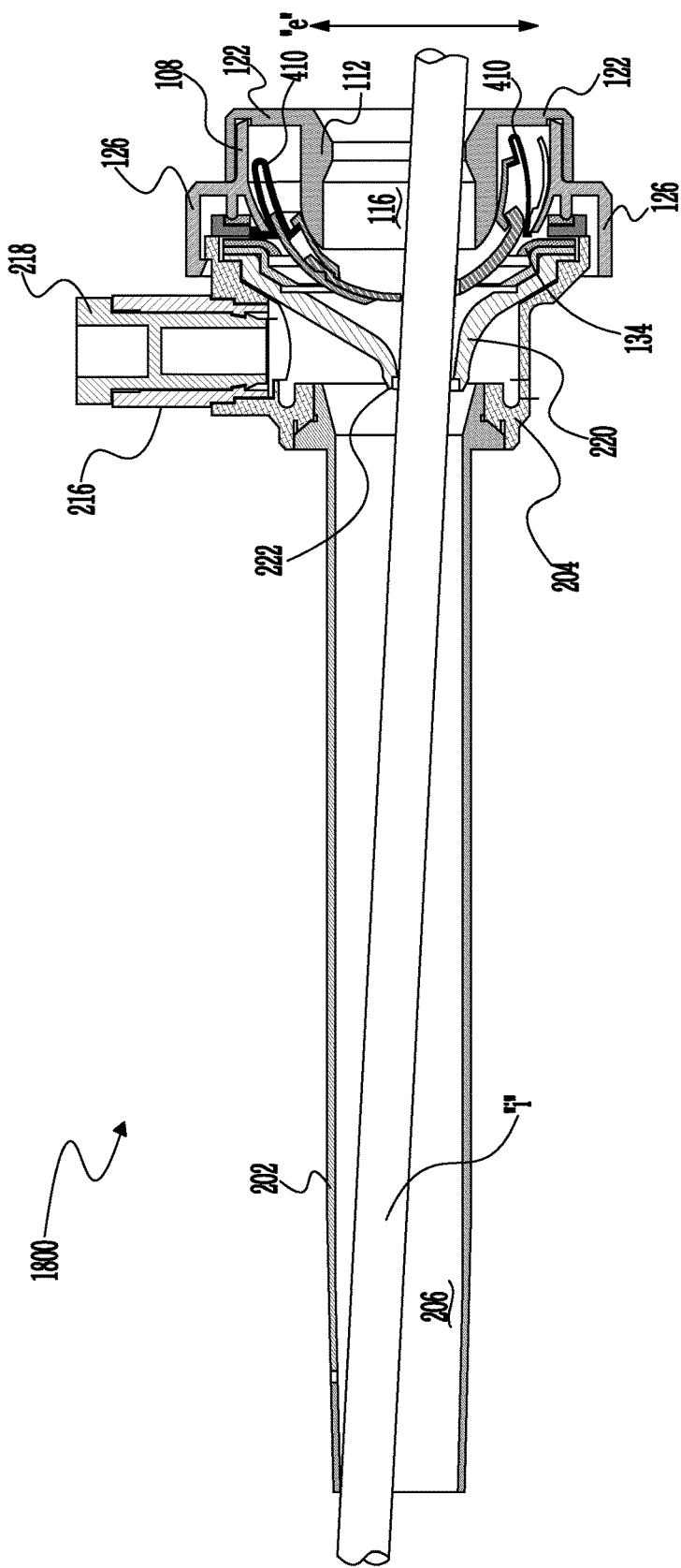
FIG. 18 is a side cross-sectional view of the cannula and seal assemblies illustrating a range of movement of the surgical instrument, in accordance with the embodiments of the present disclosure.

Additionally, with reference to FIGS. 4A and 4B, it is noted that the top portion of the seal assembly 100 includes angled portions 175 for enabling angular insertion of instruments "i," see FIGS. 17 and 18. The angulation allows for easier insertion and manipulation of instruments inserted therethrough.

Figure 5:
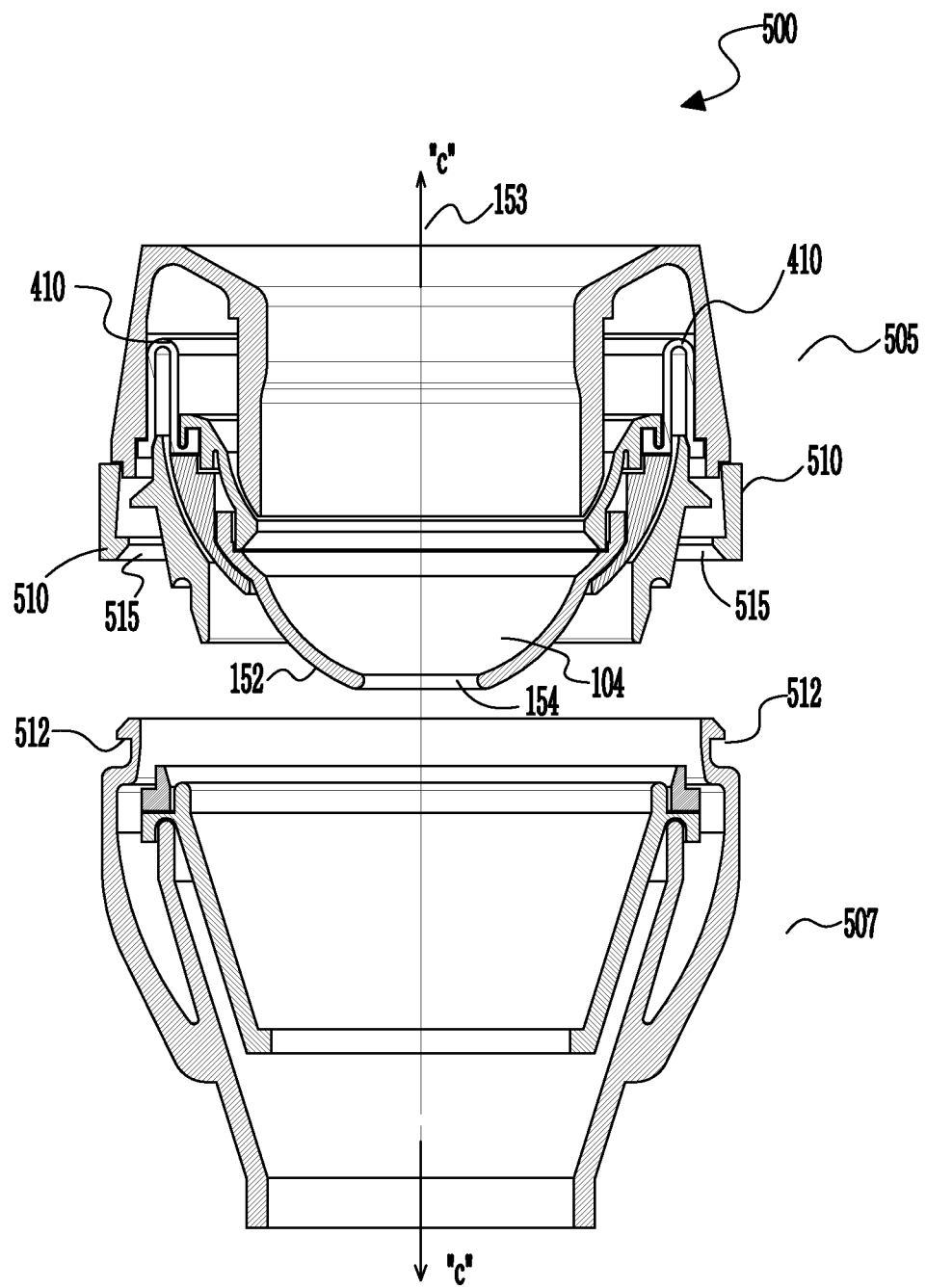
FIG. 5 illustrates a side cross-sectional view of the cannula and seal assemblies illustrating the gimbal mount, where the cannula and seal assemblies are disconnected from each other, in accordance with an embodiment of the present disclosure.

Referring to FIG. 5, a side cross-sectional view 500 of the cannula and seal assemblies 100, 200 illustrating the gimbal mount 104, where the cannula and seal assemblies 100, 200 are disconnected from each other, in accordance with an embodiment of the present disclosure is presented.

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock or like mechanical means. As previously discussed, proximal and distal housing components 106, 108 (see FIG. 3) may define an upper housing component 505, which is mountable directly to cannula assembly 200. The upper housing component 505 may be separated from the lower housing component 507. The upper housing component 505 may include one or more first projection members 510. The lower housing member 507 may include one or more second projection members 512, such as snap-fit components. The one or more first projection members 510 cooperate or frictionally engage with the one or more second projection members 512 in order to connect the upper housing portion 505 to the lower housing portion 507. The one or more second projection members 512 may be inserted into openings 515 of the upper housing component 505 in order to affix or connect to the one or more first projection members 510. The openings 515 may be adapted and dimensioned to secure and maintain the one or more second projection members 512 in place, such that upper housing component 505 and lower housing component 507 are securely affixed to each other.

As such, a user may interchange the upper housing component 505 with any other upper housing components having a variety of different rubber bellows based on the surgical procedure to be performed. Additionally, the user may interchange the lower housing component 507 with any other lower housing components including any type of seal therein (e.g., a duck bill seal, as discussed below with reference to FIGS. 15A-15C). Therefore, the attachability/detachability of the upper and lower housing components 505, 507 enables system flexibility by allowing the user to select different seal and/or rubber bellows combinations for a variety of different surgical procedures.

Figure 6A:
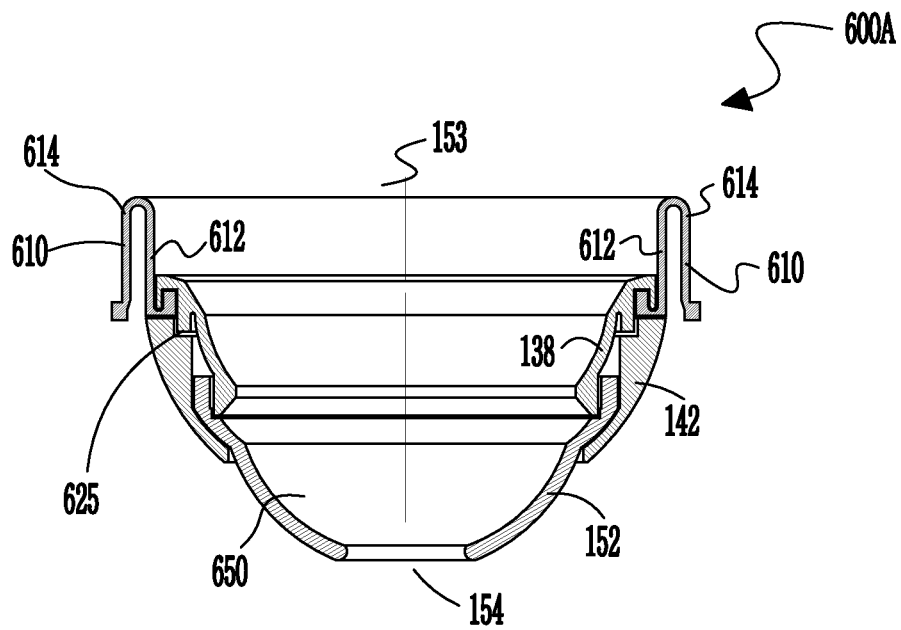
FIG. 6A is a side cross-sectional view of the gimbal mount, where the bellows seal has a uniform wall thickness, in accordance with an embodiment of the present disclosure.

Referring to FIG. 6A, a side cross-sectional view 600A of the gimbal mount 104, where rubber bellows 610 have a uniform wall thickness, in accordance with an embodiment of the present disclosure is presented.

As shown in FIG. 6A, the gimbal mount 650 has a parabolic configuration. Rubber bellows 610 have a uniform wall thickness across the circumferential length of the gimbal mount 650. In one example, the wall thickness may be 0.01 inches. Of course one skilled in the art may contemplate a variety of different thicknesses for the wall of rubber bellows 610. In the instant case, the inner wall portion 612 of rubber bellows 610 are equal in thickness to the outer wall portion 614 of rubber bellows 610. As the thickness of inner wall portion 612 and outer wall portion 614 is reduced, the amount of resistance of moving an instrument (see FIGS. 17 and 18) off axis is also decreased. As such, there is a direct relationship between the thickness of the walls 612, 614 of rubber bellows 610 and the maneuverability of an instrument inserted through opening 153.

Moreover, the gimbal mount 650 is held together (i.e., gimbal housings 138, 140) with a weld connection at, for example, weld point 625. Of course one skilled in the art may contemplate a plurality of weld points positioned across the top, bottom or central circumferential lengths of the gimbal mount 650. These weld points may take on a plurality of shapes and designs for holding together the gimbal housings 138, 140. Additionally, the parabolic configuration of the gimbal mount 650 creates a larger radius locally compared to a spherical or hemispherical configuration (as described below with reference to FIG. 6B). This change in shape results in a reduction of the angle the gimbal mount 650 requires to pivot through for the instrument seal member 142 to be tangent to the cannula assembly 200.

Figure 6B:
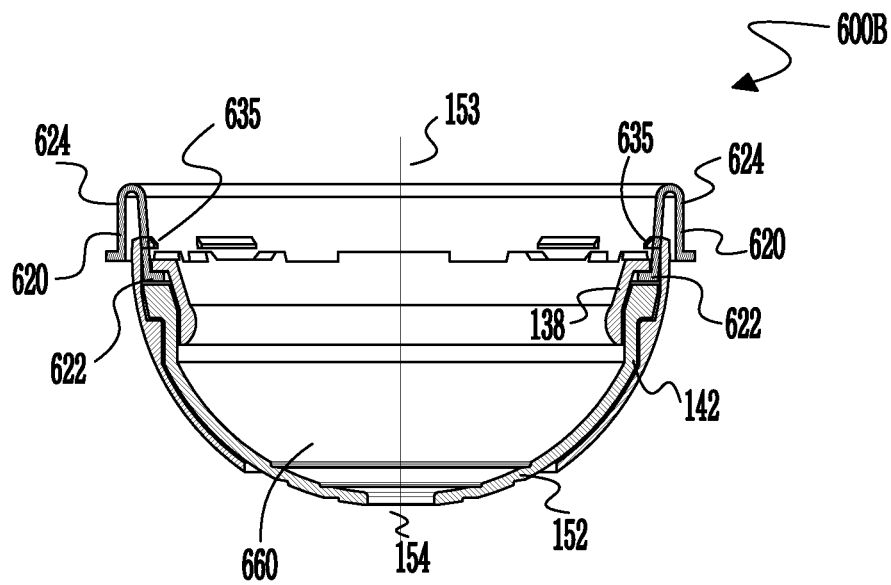
FIG. 6B is a side cross-sectional view of the gimbal mount, where the gimbal mount is held together with twist locking features, in accordance with another embodiment of the present disclosure.
Figure 11:
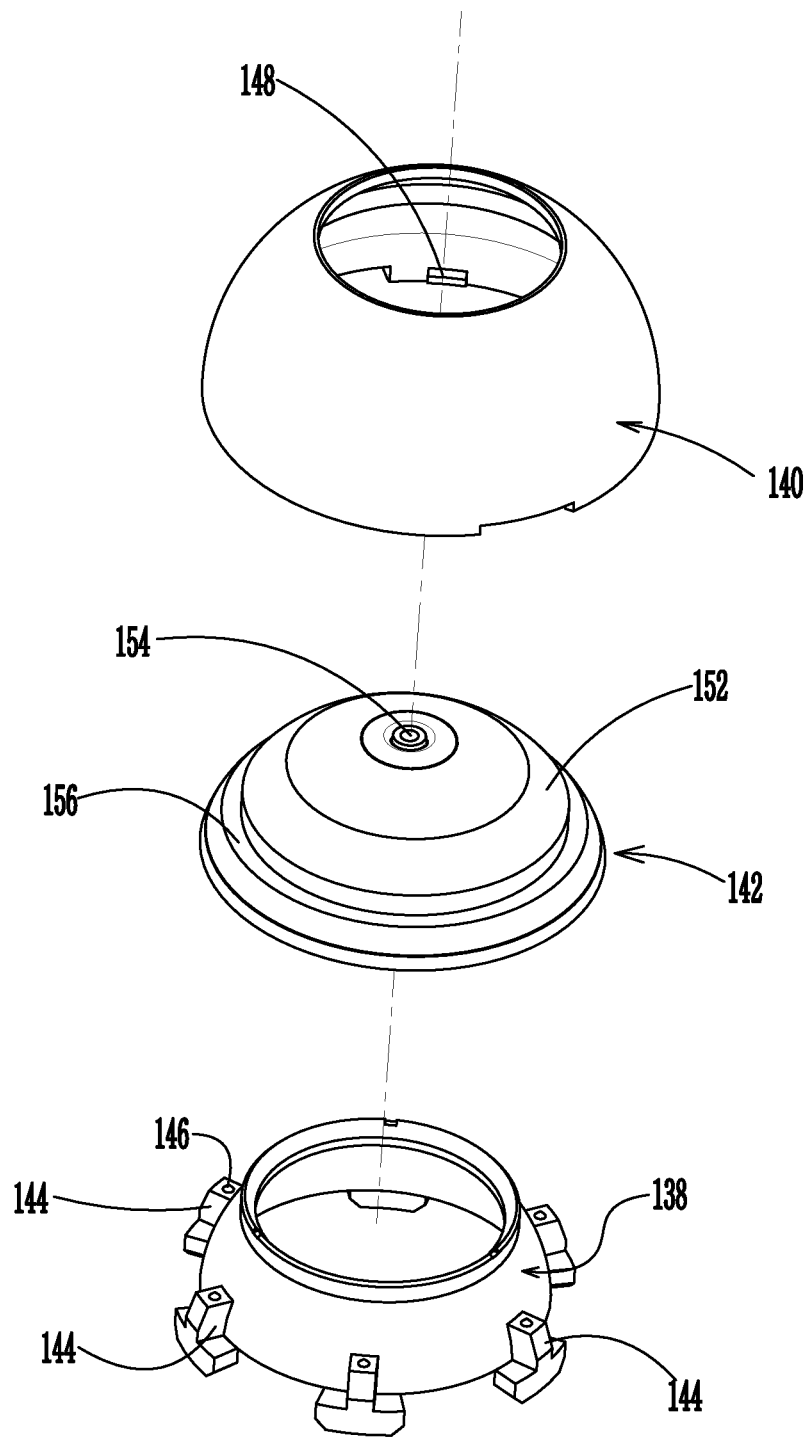
FIG. 11 is a perspective view illustrating the components of the gimbal mount, in accordance with the embodiments of FIGS. 4A-10.

Referring to FIG. 6B, a side cross-sectional view 600B of the gimbal mount 660, where the gimbal mount 660 is held together with twist locking features 635, in accordance with another embodiment of the present disclosure is presented.

As shown in FIG. 6B, the gimbal mount 660 has a hemispherical configuration. Rubber bellows 620 have a uniform wall thickness across the circumferential length of the gimbal mount 660. In one example, the wall thickness may be 0.01 inches. Of course one skilled in the art may contemplate a variety of different thicknesses for the wall of rubber bellows 620. In the instant case, the inner wall portion 622 of rubber bellows 620 is equal in thickness to the outer wall portion 624 of rubber bellows 620. However, the length of the inner wall portion 622 may be different than the length of the outer wall portion 624. For example, in the instant case, the length of the inner wall portion 622 may be greater than the length of the outer wall portion 624. Of course, in another exemplary embodiment, the opposite may also be true, where the length of the outer wall portion 624 may be greater than the length of the inner wall portion 622. As such, the twist locking features 635 may provide for a better attachment of the gimbal housings 138, 140 because a larger portion of rubber bellows 620 extends beyond the twist locking feature 635 to create a firmer and more stable grip. Thus, rubber bellows 620 may better deform or cooperate with the twist locking features 635 to maintain a secure connection between the gimbal housings 138, 140. In one exemplary embodiment, a plurality of twist locking features 635 may be circumferentially placed around several different portions of the gimbal mount 660.

Referring now to FIGS. 7-11, in conjunction with FIGS. 4A-6B, the components of gimbal mount 104 will be discussed in further detail. Gimbal mount 104 includes first and second gimbal housings 138, 140 and resilient seal member 142 (see FIG. 11), which is mounted between the housings 138, 140. In a preferred arrangement, first and second gimbal housings 138, 140 and seal member 142 each define a general hemispherical configuration as shown. First gimbal housing 138 is preferably seated within second gimbal housing 140 and secured to the second gimbal housing 140 through a snap fit connection or the like. Preferably, first gimbal housing 138 includes a plurality of mounting legs 144 radially spaced about the outer periphery of the housing component. Legs 144 define locking surfaces 146 which extend in general transverse relation to the axis "b" of seal assembly 100.

Similarly, second gimbal housing 140 includes a plurality of corresponding locking detents 148 spaced about the interior of the housing 140. Upon insertion of first gimbal housing 138 within second gimbal housing 140, mounting legs 144 slide along locking detents 148 whereby upon clearing the detents 148, locking surfaces 146 of the mounting legs 146 securely engage the locking detents 148 to fix first gimbal housing 138 within second gimbal housing 140 and securing resilient seal member 142 between the components in sandwiched relation. As appreciated, first gimbal housing 138 may be sufficiently resilient to deflect upon insertion to permit mounting legs 144 to clear locking detents 148 and return to their initial position to engage the detents 148.

As mentioned hereinabove, seal member 142 of gimbal mount 104 is secured in interposed relation between first and second gimbal housings 138, 140. Seal member 142 preferably comprises a resilient center material (e.g., polyisoprene or natural rubber) with first and second layers of fabric 150,152 impregnated on the respective proximal and distal surfaces of the resilient center material. Fabric may be of any suitable fabric for example, a SPANDEX material containing about 20% LYCRA and about 80% NYLON available from Milliken. Seal member 142 defines central aperture 154 for sealed reception of a surgical instrument.

In a preferred arrangement, first layer 150 is arranged to extend or overlap into aperture 154. In this manner, the fabric (which is stronger relative to the resilient material) is positioned to engage the surgical instrument upon passage through aperture 154 of seal member 142 thereby protecting the resilient material defining the aperture. This advantageously minimizes the potential of piercing, penetrating or tearing of the resilient material by the instrument. Alternatively, an additional layer of fabric 151 on the proximal surface of seal member 142 may be superposed and arranged to drape within aperture 154. Seal member 142 includes an annular depression 156 (see FIG. 9) on its distal surface, i.e., within second layer 152 of fabric. Depression 156 receives ledge 158 (see FIG. 10) of second gimbal housing 140 to facilitate fixation of seal member 142 between first and second gimbal housings 138, 140.

Although seal member 142 is disclosed as an impregnated fabric arrangement, it is appreciated that other seal types may be used and still achieve the objectives of the present disclosure. Further, FIG. 8 illustrates annular depressions 153, 155 which have been pressed by a molding tool into layer 153. One or more similar depressions may be pressed into layer 150 to assist positioning of fabric during manufacture of seal member 142.

Figure 14:
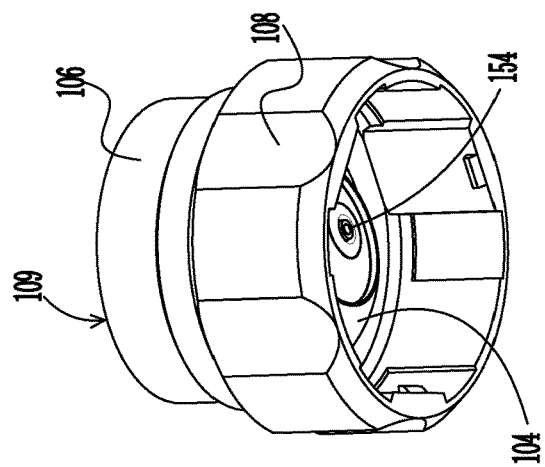
FIGS. 12-14 are perspective views illustrating the range of movement of the gimbal mount within the seal housing, in accordance with the embodiments of FIGS. 4A-11.
Figure 13:
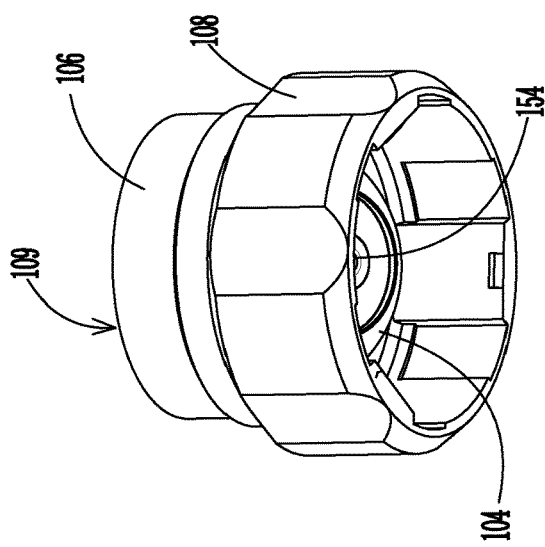
Figure 12:
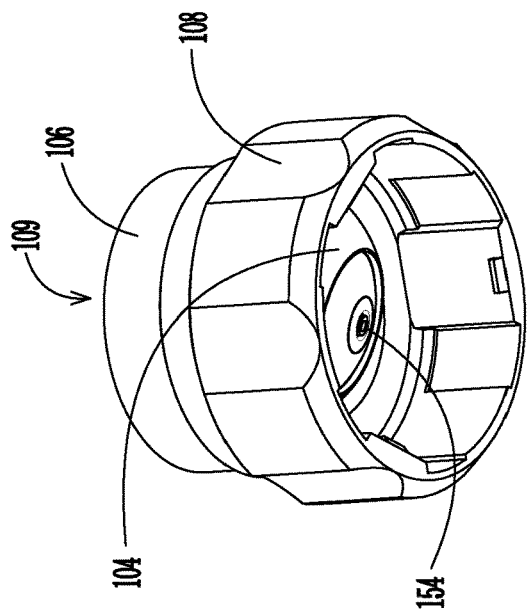

With reference now to FIGS. 12-14, in conjunction with FIGS. 4A-6B, gimbal mount 104 is free to move within the annular space 134 defined between inner and outer walls 112, 114 to permit angulation of the instrument relative to the seal axis "b" while still maintaining a seal thereabout. Specifically, gimbal mount 104 is adapted for swiveling movement about a center of rotation "c" which is coincident with the axis of seal assembly 100. In this regard, the axis of the aperture 154 of seal member 142 intersects the axis "b" of the seal assembly 100 during angulation of the instrument. During angulation, gimbal mount 104 is in contact with bellows 410 (see FIGS. 4A, 4B) attached to a side wall of the seal housing 102.

In a preferred arrangement, gimbal mount 104 may angulate or rotate through an angle inclusive of about 25°, more preferably about 22.5° relative to seal axis "b." An annular stop (not shown) may further restrict angulation by a couple of degrees of movement to be inclusive of an angle of about 19° relative to axis "b."

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock or like mechanical means. As previously discussed, proximal and distal housing components 106, 108 may define an upper housing component 109 which is mountable directly to cannula assembly 200. Alternatively, inner housing portion 110 which defines a lower housing component may be directly mounted to cannula assembly 200 independent of the upper housing component 109. Specifically, the lower housing component 110 which houses gimbal mount 104 may be mounted to cannula assembly independent of the remaining housing components. The upper housing may then be mounted to lower housing or cannula assembly 200 as needed. Even further, upper housing component 109 may be mounted to cannula assembly 200 without lower housing component 110. Other means of joining seal assembly 100 to cannula assembly 200 will be readily apparent to one of ordinary skill in the art.

Figure 15A:
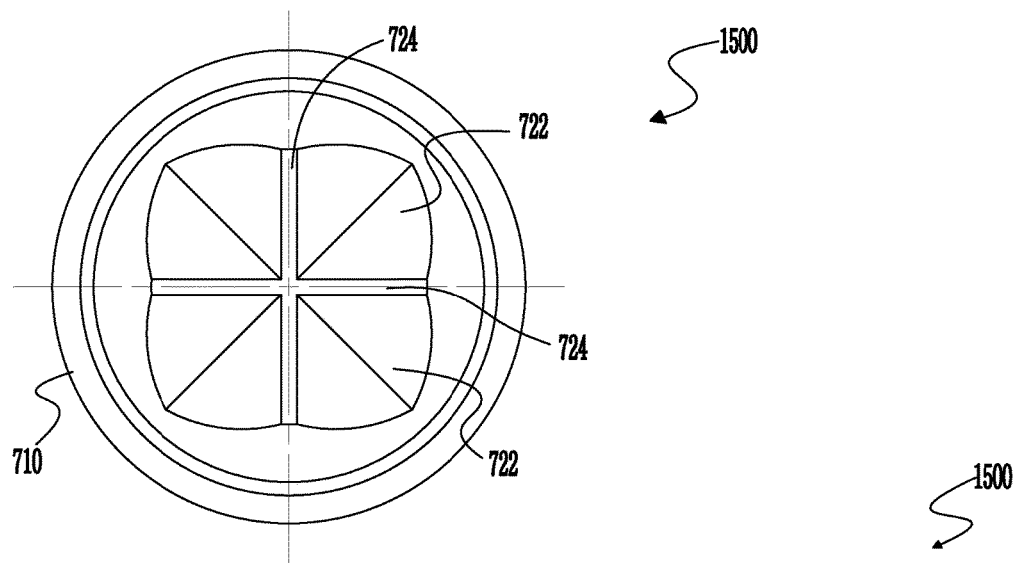
FIGS. 15A-15C are top, side, and perspective views, respectively, of a duck bill seal, in accordance with an embodiment of the present disclosure.
Figure 15B:
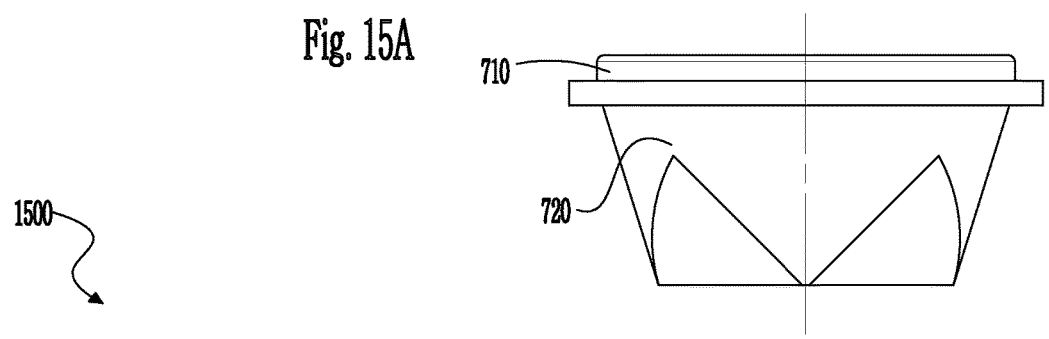
Figure 15C:
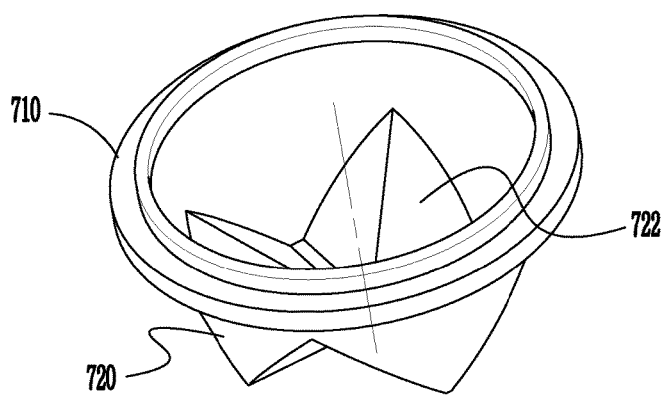

Referring to FIGS. 15A-15C, top, side, and perspective views 1500 of a duck bill seal, in accordance with an embodiment of the present disclosure are presented.

The duckbill seal 1500 is configured to prevent loss of insufflation gas when no instrument is inserted through opening 153 of seal assembly 100 (see FIG. 1). As best shown in FIG. 15C, the duckbill seal 1500 includes an upper member 710 and a lower member 720. The lower member 720 may include an irregular shaped bottom segment 722. As shown in FIG. 15A, the duckbill seal 1500 also defines a slit 724, shaped in a "+" configuration on the bottom segment 722. Of course one skilled in the art may contemplate a plurality of different slit configurations suitable for the reception and securement of an instrument. Air pressure from insufflation causes the slit 724 to close, thus creating a secure seal when no instrument is inserted therethrough. The duckbill seal 1500 may be positioned within the cannula assembly 200, as illustrated in FIG. 1, such that the duckbill seal 1500 seals the cannula assembly 200 directly to the gimbal mount 104 (see FIGS. 4, 4B). Moreover, the duckbill seal 1500 may be tapered to allow the cannula assembly 200 to have a reduced diameter.

In an alternative embodiment, the seal member may be frusto-conical in shape and define an aperture for sealed reception of the instrument. In the alternative, seal member may be a flat disc-shaped valve, balloon valve, flapper valve, etc. The seal member may comprise a flat disc-shaped, conical, or hourglass-shaped member including a fabric material molded with an elastomer. In a further alternative, seal member may be a fabric seal and may be desirably arranged so as to have a constriction. A preferred material is a synthetic material such as nylon, Kevlar® or any other material that will expand and compress about an instrument inserted therethrough. The fabric may have a coating of urethane, silicon or other flexible lubricious materials to facilitate passage of an instrument or other object through the seal member.

Figure 16:
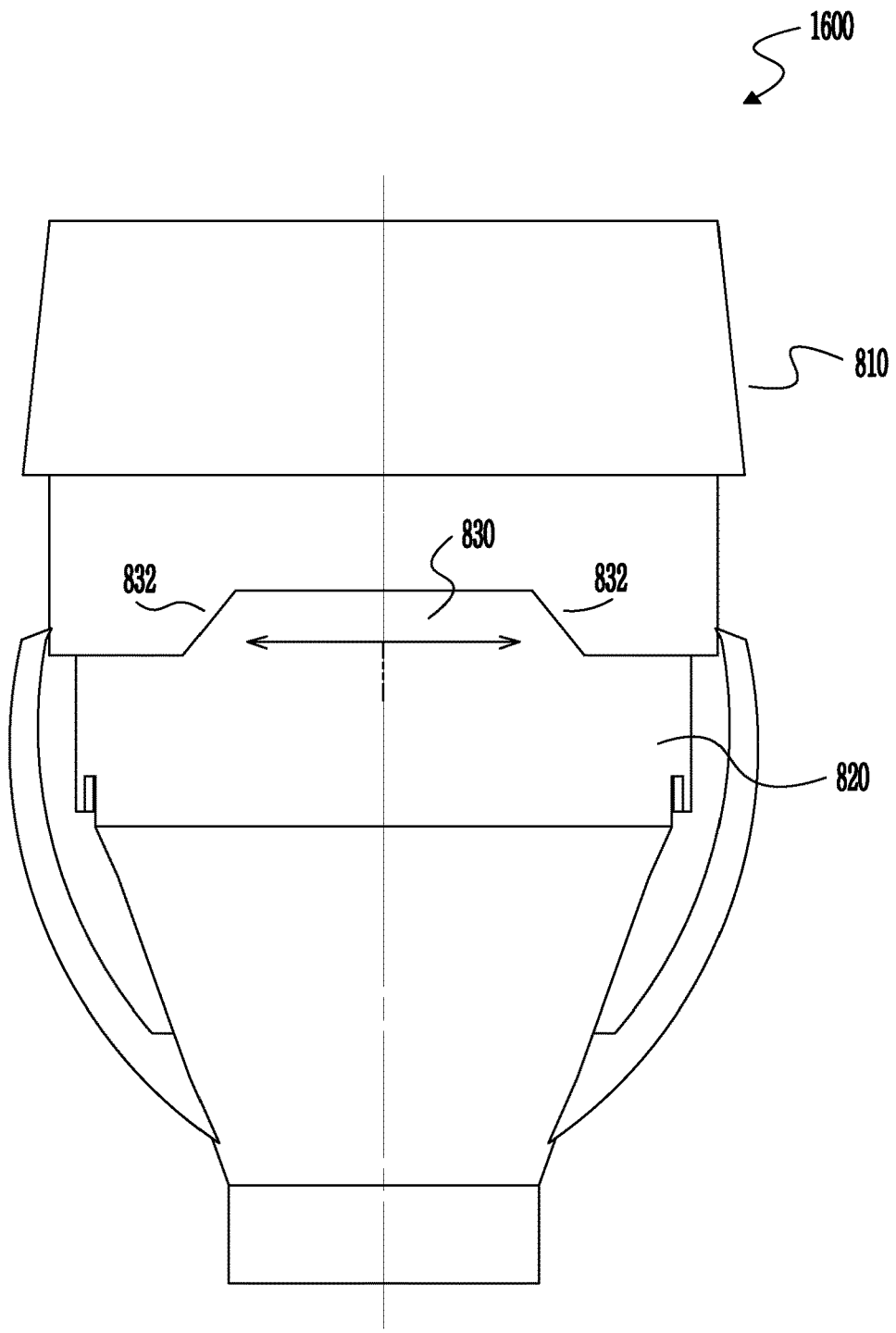
FIG. 16 is a side view of a gimbal housing depicting an overlapping piece with angled sides, in accordance with another embodiment of the present disclosure.

Referring to FIG. 16, a side view 1600 of a gimbal housing 820 depicting an overlapping piece 830 with angled sides 832, in accordance with another embodiment of the present disclosure is presented.

FIG. 16 illustrates an overlapping piece 830 having angled sides 832 configured to aid in the alignment of the gimbal housing 810 to cannula assembly 820. Overlapping piece 830 provides for additional stability between the gimbal housing 810 and the cannula assembly 820, such that instruments inserted therethrough are stabilized during surgical procedures without the loss of insufflation gases.

Referring now to FIGS. 17-18, use of the seal assembly 100 and cannula assembly 200 in connection with introduction of a surgical instrument will be discussed. FIG. 17 illustrates a perspective view 1700 of an instrument "i" introduced through the seal assembly 100 connected to the cannula assembly 200. FIG. 18 illustrates a side cross-sectional view 1800 of the instrument "i" inserted through the seal assembly 100 connected to the cannula assembly 200.

Seal assembly 100 is mounted to cannula assembly 200, which was previously introduced into an insufflated abdominal cavity. An instrument "i" is inserted into seal assembly 100 through passage 116 of inner cylindrical guide wall 112 in seal housing 102. If the axis of the instrument "i" is not perfectly aligned with the axis "a" of cannula assembly 200 or axis "b" of seal assembly 100, then the surgical instrument contacts the inner guide wall 112 and/or the inner surface of seal member 142. Contact with the seal member 142 may cause some deformation of the seal member 142. The instrument "i" slides along the surface of the gimbal mount 104 and/or the seal member 142, to the aperture 154. Aperture 154 stretches to accommodate the instrument diameter, as necessary.

The instrument "i" passes further distally into the cannula housing 204 passing through duckbill valve 220 and cannula sleeve 202 into the body cavity. Once the instrument "i" is disposed within aperture 154, gimbal mount 104 and arcuate surface 118 is overcome, gimbal mount 104 swivels with respect to seal housing 102 as the instrument "i" is manipulated. The gimbal mount 104 is free to swivel relative to housing 102, while allowing seal member 142 to maintain sealing engagement with the instrument "i" passed therethrough, as well as maintaining the seal around the gimbal mount 104. Preferably, the seal member 142 includes resilient material and fabric material, which resists deformation of aperture 154, as well as tearing of seal member 142.

Moreover, cannula housing 204 may include port opening 214 and luer fitting 216 positioned within the port opening 214. Luer fitting 216 is adapted for connection to a supply of insufflation gas and incorporates valve 218 (see FIG. 17) to selectively open and close the passage of the luer fitting 216. Cannula housing 204 further includes duckbill or zero closure valve 220 (see FIG. 18), which tapers distally and inwardly to a sealed configuration. Closure valve 220 defines a slit 222, which opens to permit passage of the surgical instrumentation and closes in the absence of the instrumentation. Closure valve 220 is preferably adapted to close upon exposure to the forces exerted by the insufflation gases in the internal cavity. Other zero closure valves are also contemplated, including single or multiple slit valve arrangements, trumpet valves, flapper valves, etc.

In operation or use, as the instrument "i" is moved up and down axis "e," rubber bellows 410 maintain the instrument "i" in its biased position, as desired by the user. The biased position is an off-center positioned with respect to axes "a," "b" or "c," as illustrated in FIGS. 1-6B. When the instrument "i" is removed from the seal assembly 100 and cannula assembly 200, rubber bellows 410 re-position the gimbal mount 104 back to its centered and unbiased position. The unbiased position is a substantially central position with respect to axes "a," "b" or "c," as illustrated, for example, in FIG. 4A. Thus, rubber bellows 410 act to negate the displacement caused by the insertion of one or more surgical instruments through the cannula assembly 100 and the seal assembly 200. Stated differently, gimbal mount 104 is re-positioned to its initial unbiased position, where the gimbal mount 104 is coaxial with axes "a" or "b" defined by the cannula assembly 100 and the seal assembly 200. Additionally, rubber bellows 410 seal the gimbal mount 104 to the seal assembly 100 and allow for rotation or swiveling of the gimbal mount 104. Furthermore, rubber bellows 410 may cooperate with the cannula assembly 200 in a plurality of separate and distinct sealing points across the circumference or periphery of the gimbal mount 104 in order to create a secure seal between the sealing assembly 100 and the cannula assembly 200.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical access device, comprising:
    a seal assembly including (i) a seal housing having an upper housing portion and a lower housing portion and (ii) a gimbal mount disposed within the seal housing and in a continuous frictional relationship with the upper and lower housing portions of the seal housing, the gimbal mount having first and second gimbal housings, the seal housing defining a central longitudinal axis and having a longitudinal passage for receiving at least one surgical object therethrough and the gimbal mount adapted for angular movement relative to the central longitudinal axis; and a bellows circumferentially positioned on a proximal end of the gimbal mount such that the bellows sits over the gimbal mount, the bellows dimensioned and adapted to establish a biasing relationship with the gimbal mount such that the bellows overcomes the frictional relationship between the gimbal mount and the seal housing to permit the gimbal mount to align with the central longitudinal axis;

wherein one end of the bellows is secured between the first gimbal housing and the second gimbal housing, and another end of the bellows is secured between the upper housing portion and the lower housing portion, the first gimbal housing, the second gimbal housing, and a seal member cooperate to form the gimbal mount.

2. The surgical access device according to claim 1, wherein the gimbal mount defines a substantially hemispherical configuration.

3. The surgical access device according to claim 1, wherein the gimbal mount defines a substantially parabolic configuration.

4. The surgical access device according to claim 1, wherein the upper housing portion of the seal housing mechanically cooperates with the bellows.

5. The surgical access device according to claim 4, wherein the upper seal housing defines an angular opening therethrough to facilitate angular reception of the at least one surgical object.

6. The surgical access device according to claim 1, wherein the bellows is dimensioned and adapted to prevent passage of fluids through the seal housing.

7. The surgical access device according to claim 1, wherein the bellows has a uniform wall thickness of about 0.01 inches.

8. The surgical access device according to claim 1, wherein the bellows is positioned within a space such that the gimbal mount is movable relative to the seal housing, the space defined between an inner wall and an outer wall of the seal housing.

9. The surgical access device according to claim 1, wherein the bellows is dimensioned and configured to create a plurality of sealing points between the seal housing and the gimbal mount.

10. The surgical access device according to claim 1, wherein a cannula assembly detachably connects to the gimbal mount via a plurality of sealing points.

11. The surgical access device according to claim 10, wherein the cannula assembly includes a duck bill seal configured to receive the gimbal mount and prevent loss of insufflation gas when no surgical object is inserted through the longitudinal passage of the seal housing.

12. The surgical access device according to claim 11, wherein the duck bill seal is dimensioned and configured to be tapered to allow the cannula assembly to have a reduced diameter.

13. The surgical access device according to claim 11, wherein the seal housing is adapted to be detachably mounted to a cannula housing of the cannula assembly including the duck bill seal for providing a substantially fluid-tight seal when the at least one surgical object is inserted into the seal assembly and through the cannula assembly.

14. The surgical access device according to claim 1, wherein the bellows sits over the gimbal mount when the at least one surgical object is received through the longitudinal passage to access a body cavity.

15. A seal assembly comprising:

a seal housing defining a central longitudinal axis and having a longitudinal passage for receiving at least one surgical object therethrough; and a gimbal mount disposed within the seal housing and defining a hemispherical configuration, the gimbal mount being in frictional engagement with the seal housing and adapted for angular movement relative to the central longitudinal axis; and a bellows circumferentially positioned on a proximal end of the gimbal mount, the bellows being configured to establish a biasing relationship with the gimbal mount such that the bellows overcomes the frictional engagement between the gimbal mount and the seal housing to permit the gimbal mount to align with the central longitudinal axis.

16. The seal assembly of claim 15, wherein the seal housing includes an upper housing portion and a lower housing portion and the gimbal mount includes first and second gimbal housings.

17. The seal assembly of claim 16, wherein one end of the bellows is secured between the first gimbal housing and the second gimbal housing, and another end of the bellows is secured between the upper housing portion and the lower housing portion.

18. The seal assembly of claim 16, wherein the gimbal mount further includes a seal member.

19. The seal assembly of claim 15, wherein the bellows is dimensioned and adapted to prevent passage of fluids through the seal housing.

\* \* \* \* \*